(12) United States Patent
Hulin

(10) Patent No.: US 6,812,350 B2
(45) Date of Patent: Nov. 2, 2004

(54) SYNTHESIS OF 3,3,4,4-TETRAFLUOROPYRROLIDINE AND NOVEL DIPEPTIDYL PEPTIDASE-IV INHIBITOR COMPOUNDS

(75) Inventor: Bernard Hulin, Essex, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/455,747

(22) Filed: Jun. 3, 2003

(65) Prior Publication Data

US 2004/0002609 A1 Jan. 1, 2004

Related U.S. Application Data

(60) Provisional application No. 60/386,112, filed on Jun. 4, 2002.

(51) Int. Cl.$^7$ .............................................. C07D 205/04
(52) U.S. Cl. .................... 548/540; 546/156; 548/314.4; 562/433; 558/385; 558/430
(58) Field of Search ......................................... 548/540

(56) References Cited

U.S. PATENT DOCUMENTS 6,710,040 B1 * 3/2004 Hulin et al. ........... 514/210.17

OTHER PUBLICATIONS

Bhuniya et al. J. Org. Chem. 1996, 61:6108–6113.*
Barlow et al. J. Med. Chem. 1991, 34(11): 3149–3158.*
Chaudry et al., J. Chem. Soc. 1964, p. 874.

International Preliminary Examining Authority PCT Written Opinion for corresponding International Application PCT/IB03/02259.

Bhuriya et al., J. Org. Chem., vol. 61, 1996, pp. 6108–6113.

Barlow et al., J. Med. Chem., vol. 34, No. 11, 1991, pp. 3149–3158.

Brown et al., J. Am. Chem. Soc., vol. 114, 1992, pp. 3092–3098.

* cited by examiner

*Primary Examiner*—Evelyn Mei Huang
(74) *Attorney, Agent, or Firm*—Peter C. Richardson; Gregg C. Benson; William F. Mulholland

(57) ABSTRACT

The present invention relates to a method of making novel dipeptidyl peptidase-IV ("DPP-IV") inhibitor compounds useful for treating, inter alia, diseases that are associated with proteins that are subject to processing by DPP-IV, such as Type 2 diabetes mellitus, metabolic syndrome (Syndrome X or insulin resistance syndrome), hyperglycemia, impaired glucose tolerance, glucosuria, metabolic acidosis, cataracts, diabetic neuropathy, diabetic nephropathy, diabetic retinopathy, diabetic cardiomyopathy, Type 1 diabetes, obesity, hypertension, hyperlipidemia, atherosclerosis, osteoporosis, osteopenia, frailty, bone loss, bone fracture, acute coronary syndrome, infertility due to polycystic ovary syndrome, short bowel syndrome and to prevent disease progression in Type 2 diabetes. The invention also relates to a method of making 3,3,4,4-tetrafluoropyrrolidine, a starting material utilized in the afore-mentioned method for preparing DPP-IV compounds.

15 Claims, No Drawings

SYNTHESIS OF 3,3,4,4-TETRAFLUOROPYRROLIDINE AND NOVEL DIPEPTIDYL PEPTIDASE-IV INHIBITOR COMPOUNDS

This application is filed claiming priority from co-pending U.S. Provisional Application No. 60/386,112, filed Jun. 4, 2002.

FIELD OF INVENTION

The present invention relates to a method of making novel dipeptidyl peptidase-IV ("DPP-IV') inhibitor compounds and a method of making 3,3,4,4-tetrafluoropyrrolidine, a starting material utilized in the afore-mentioned method for preparing DPP-IV compounds.

BACKGROUND OF INVENTION

Dipeptidyl peptidase-IV (EC 3.4.14.5) is a serine protease that preferentially hydrolyzes an N-terminal dipeptide from proteins having proline or alanine in the 2 position. The physiological role(s) of DPP-IV have not been fully elucidated, it is believed to be involved in diabetes, glucose tolerance, obesity, appetite regulation, lipidemia, osteoporosis, neuropeptide metabolism and T-cell activation.

DPP-IV has been implicated in the control of glucose homeostasis, because its substrates include the incretin peptides glucagon-like peptide 1 (GLP-1) and gastric inhibitory polypeptide (GIP). Cleavage of the N-terminal amino acids from these peptides renders them functionally inactive. GLP-1 has been shown to be an effective anti-diabetic therapy in Type 2 diabetic patients and to reduce the meal-related insulin requirement in Type 1 diabetic patients. GLP-1 is believed to regulate satiety, lipidemia and osteogenesis. Exogenous GLP-1 has been proposed as a treatment for patients suffering from acute coronary syndrome, angina and ischemic heart disease.

Administration of DPP-IV inhibitors in vivo prevents N-terminal degradation of GLP-1 and GIP, resulting in higher circulating concentrations of these peptides, increased insulin secretion and improved glucose tolerance. On the basis of these observations, DPP-IV inhibitors are regarded as agents for the treatment of Type 2 diabetes, a disease in which glucose tolerance is impaired.

In spite of the early discovery of insulin and its subsequent widespread use in the treatment of diabetes, and the later discovery of and use of sulfonylureas (e.g. chlorpropamide (Pfizer), tolbutamide (Upjohn), acetohexamide (E.I. Lilly)), biguanides (Phenformin (Ciba Geigy), Mefformin (G.D. Searle)) and thiazolidinediones (rosiglitazone (GlaxoSmithKline, Bristol-MyersSquibb), pioglitazone (Takeda, E.I. Lilly)) as oral hypoglycemic agents, the treatment of diabetes remains less than satisfactory.

The use of insulin, necessary in Type 1 diabetic patients and about 10% of Type 2 diabetic patients in whom currently available oral hypoglycemic agents are ineffective, requires multiple daily doses, usually by self-injection. Determination of the appropriate dosage of insulin necessitates frequent estimations of the glucose concentration in urine or blood. The administration of an excess dose of insulin causes hypoglycemia, with consequences ranging from mild abnormalities in blood glucose to coma, or even death.

Treatment of Type 2 diabetes usually comprises a combination of diet, exercise, oral agents, and in more severe cases, insulin. However, the clinically available hypoglycemics can have side effects which limit their use. A continuing need for hypoglycemic agents, which may have fewer side effects or succeed where others fail, is clearly evident.

Poorly controlled hyperglycemia is a direct cause of the multiplicity of complications (cataracts, neuropathy, nephropathy, retinopathy, cardiomyopathy) that characterize advanced diabetes mellitus. In addition, diabetes mellitus is a comorbid disease that frequently confounds hyperlipidemia, atherosclerosis and hypertension, adding significantly to the overall morbidity and mortality attributable to those diseases.

Epidemiological evidence has firmly established hyperlipidemia as a primary risk factor for cardiovascular disease ("CVD") due to atherosclerosis. Atherosclerosis is recognized to be a leading cause of death in the United States and Western Europe. CVD is especially prevalent among diabetic subjects, at least in part because of the existence of multiple independent risk factors such as glucose intolerance, left ventricular hypertrophy and hypertension in this population. Successful treatment of hyperlipidemia in the general population, and in diabetic subjects in particular, is therefore of exceptional medical importance.

Hypertension (or high blood pressure) is a condition that can occur in many patients in whom the causative agent or disorder is unknown. Such "essential" hypertension is often associated with disorders such as obesity, diabetes and hypertriglyceridemia, and it is known that hypertension is positively associated with heart failure, renal failure and stroke. Hypertension can also contribute to the development of atherosclerosis and coronary disease. Hypertension, together with insulin resistance and hyperlipidemia, comprise the constellation of symptoms that characterize Metabolic Syndrome, also known as insulin resistance syndrome ("IRS") and syndrome X.

Obesity is a well-known and common risk factor for the development of atherosclerosis, hypertension and diabetes. The incidence of obesity and hence of these diseases is increasing worldwide. Currently few pharmacological agents are available that reduce adiposity effectively and acceptably.

Osteoporosis is a progressive systemic disease characterized by low bone density and microarchitectural deterioration of bone tissue, with a consequent increase in bone fragility and susceptibility to fracture. Osteoporosis and the consequences of compromised bone strength are a significant cause of frailty, and of increased morbidity and mortality.

Heart disease is a major health problem throughout the world. Myocardial infarctions are a significant source of mortality among those individuals with heart disease. Acute coronary syndrome denotes patients who have or are at high risk of developing an acute myocardial infarction (MI).

Though there are therapies available for the treatment of diabetes, hyperglycemia, hyperlipidemia, hypertension, obesity and osteoporosis there is a continuing need for alternative and improved therapies. 3,3,4,4-tetrafluoropyrrolidine is a starting material utilized in the preparation of the particular DPP-IV inhibitor compounds described herein. A synthesis of 3,3,4,4-tetrafluoropyrrolidine was described in the following reference: Chaudhry et al. *J.Chem.Soc.* 1964; 874.

SUMMARY OF INVENTION

This invention is directed to a process for preparing a compound of Formula I,

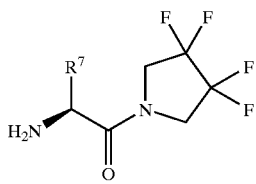

wherein $R^7$ is $(C_1-C_8)$alkyl or $(C_3-C_8)$cycloalkyl, comprising:

a) treating an N-protected amino acid of the formula II,

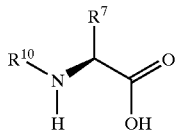

wherein $R^7$ is $(C_1-C_8)$alkyl or $(C_3-C_8)$cycloalkyl and $R^{10}$ is a nitrogen-protecting group, with a base and 3,3,4,4-tetrafluoropyrrolidine hydrochloride in the presence of a coupling agent to form a coupled amino acid intermediate; and b) deprotecting the coupled amino acid intermediate to form a compound of Formula I.

In a preferred embodiment, $R^{10}$ is tert-butoxycarbonyl, benzyloxycarbonyl or fluorenylmethoxycarbonyl.

In another preferred embodiment, the N-protected amino acid is (L)-Boc-isoleucine, (L)-Boc-cyclohexylgycine, (L)-Boc-allo-isoleucine, (L)-Boc-leucine, (L)-Boc-valine or (L)-Boc-alanine.

In another embodiment, the coupling agent is 1-(-3-dimethylaminopropyl)-3-ethylcarbodiimide hydrochloride, dicyclohexylcarbodiimide, 2-ethoxy-1-ethoxycarbonyl-1,2-dihydroquinoline, carbonyldiimidazole or diethylphosphorylcyanide.

In another embodiment, the base in step (a) is triethylamine.

In a preferred embodiment, the coupled amino acid intermediate is deprotected with gaseous hydrochloric acid.

In another preferred embodiment, the coupled amino acid intermediate of step (a) is purified.

The invention is also directed to a process of making 3,3,4,4-tetrafluoropyrrolidine hydrochloride comprising:

a) treating 2,2,3,3-tetrafluorobutanediol with an activating reagent or combination of activating reagents to form a compound of Formula VI,

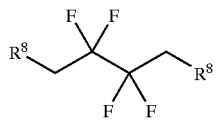

wherein $R^8$ is a leaving group;

b) reacting the compound of Formula VI with a protected primary amine, $NH_2R^9$, in a solvent, to form a compound of Formula VII;

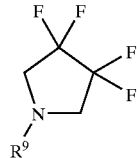

and;

c) removing the protecting group, $R^9$, from the N-protected amine to form 3,3,4,4-tetrafluoropyrrolidine or a salt thereof.

In one embodiment, the activating reagent of step (a) is HBr, $PBr_3$, $PBr_5$, $SOBr_2$ or HI, or the combination of activating reagents is trifluoromethanesulfonic anhydride/organic base, alkylsulfonyl chloride/organic base, arylsulfonyl chloride/organic base, $Ph_3P/CBr_4$, $Ph_3P/N$-bromosuccinimide, $KI/H_3PO_4$, $Ph_3P/I_2$, or $Me_3SiCl/NaI$.

In a preferred embodiment, the activating reagent combination is trifluoromethanesulfonic anhydride and an organic base.

In another preferred embodiment, the organic base is pyridine.

In another embodiment, $R^8$ is Br, I or $OSO_2R^{11}$, wherein $R^{11}$ is (1) a $C_1-C_8$ straight or branched alkyl, optionally substituted with fluorine or (2) an aryl group, optionally substituted with halogen or a $C_1-C_8$ straight or branched alkyl optionally substituted with one to four fluorines.

In a preferred embodiment, $R^8$ is trifluoromethylsulfonyloxy.

In another preferred embodiment, the N-protected amine of step (b) is benzyl amine.

In another preferred embodiment, the protecting group, $R^9$, is benzyl, tert-butyl, allyl or benzhydryl.

In a further preferred embodiment, the protecting group, $R^9$, is benzyl, and is removed in step (c) by hydrogenolysis in the presence of palladium.

As used herein, the term "leaving group" is an group wherein the bond to $R^8$ is readily cleaved by standard chemical manipulation known to those skilled in the art.

As used herein, the term "inert solvent" is a solvent whose structure does not contain functional groups likely to interfere with the reaction. Examples for the activation of the hydroxyl groups and the coupling are dichloromethane, 1,2-dichloroethane, tetrahydrofuran (THF), dimethylformamide (DMF)

As used herein, the term "activating reagent" in this instance is one that transforms a hydroxyl group into a leaving group such as bromide, iodide, alkylsulfonate or arylsulfonate.

DESCRIPTION OF INVENTION

Some of the starting compounds for the reactions described in the schemes and Examples are prepared as illustrated herein. All other starting compounds may be obtained from general commercial sources, such as Sigma-Aldrich Corporation, St. Louis, Mo.

A synthesis of 3,3,4,4-tetrafluoropyrrolidine was described in the following reference: Chaudhry et al. *J.Chem.Soc.* 1964; 874 (hereinafter "Chaudhry"), incorporated by reference in its entirety. In Scheme I, depicting the last step of the synthesis, the reduction of 2,2,3,3-tetrafluorosuccinimde with lithium aluminum hydride proceeds in 52% yield, after distillation and sublimation under reduced pressure. The sublimation technique described by Chaudhry may be useful in the case of small scale reaction, but is less practical, however, on larger scales.

SCHEME I

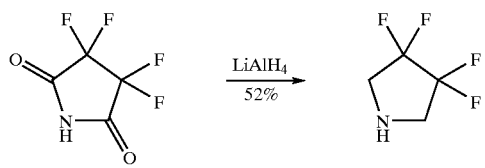

A new synthesis, as shown in Scheme II, proceeds in high yields. 3,3,4,4-tetrafluoropyrrolidine is obtained in pure form by simple filtration and trituration in the last step. It will be recognized by a person skilled in the art that the workup of this last step is more convenient and may be performed on a larger scale, compared to the Chaudhry synthesis.

SCHEME II

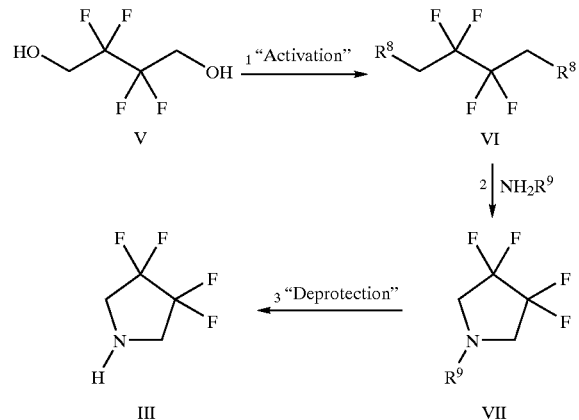

According to Scheme II, in Step 1, the hydroxyl groups of 2,2,3,3-tetrafluorobutanediol (V) are activated to a leaving group, $R^8$, (wherein $R^8$ may be Br, I or $SO_2R^{11}$, wherein $R^{11}$ may either be (1) a $C_1$–$C_8$ straight or branched alkyl, optionally substituted with one or several fluorines or (2) an aryl group, optionally substituted with halogen or a $C_1$–$C_8$ straight or branched alkyl optionally substituted with one to four fluorines). Preferably, however, $R^8$ is trifluoromethylsulfonyloxy ($F_3CSO_3$). The activating reagents necessary to transform the alcohol function to, for example, bromine or iodine are well-known to those skilled in the art (see e.g. March, Advanced Organic Chemistry, $3^{rd}$ ed. pp. 382–384 and Larock, Comprehensive Organic Transformations, pp. 353–360, incorporated by reference) and include, but are not limited to, the following activating reagents: hydrogen bromide ("HBr"), phosphorus tribromide ("$PBr_3$"), phosphorus pentabromide ("$PBr_5$"), thionyl bromide ("$SOBr_2$") and hydrogen iodide ("HI"). Suggested activating reagent combinations are triphenylphosphine/carbon tetrabromide ("$Ph_3P/CBr_4$"), $Ph_3P$/N-Bromosuccinimide, potassium iodide/phosphoric acid ("$KI/H_3PO_4$"), $Ph_3P/I_2$ and $Me_3SiCl/NaI$. Activation of the alcohol function to an alkyl or arylsulfonate is accomplished by reaction with the corresponding sulfonyl chloride or sulfonic anyhydride in an inert solvent in the presence of a base, such as pyridine or triethylamine, which is cooled (0° C.) and stirred for about one hour. The reaction mixture is then stirred at room temperature for about an additional hour.

In Step 2, the reaction of compound VI with a primary amine $R^9NH_2$, wherein $R^9$ is an alkyl or aryl "protecting" group (i.e., such that the bond linking $R^9$ to the nitrogen atom may be easily cleaved by standard chemical manipulation known to those skilled in the art in Step 3), is accomplished by heating the solution to reflux overnight. Examples of N-protecting groups are described in "Protective Groups in Organic Synthesis", $2^{nd}$. Ed., P. G. M. Wuts and T. W. Greene, p.362, incorporated herein by reference, and include, for example, benzyl, tert-butyl, allyl and benzhydryl. Preferably, $R^9$ is benzyl, in which case the deprotection, Step 3, is performed by hydrogenolysis in the presence of palladium.

Step 3 can be performed on a cationic salt of intermediate compound VII, such as hydrochloride, hydrobromide, acetate, trifluoroacetate, etc., in an appropriate solvent (e.g. water, methanol or ethanol). Removal of the $R^9$ protecting group from compound VII may be accomplished under conditions appropriate for the particular $R^9$ protecting group in use. Such conditions include, for example, (a) hydrogenolysis where $R^9$ is benzyl or benzhydryl; (b) treatment with a strong acid, such as trifluoroacetic acid or hydrochloric acid, wherein $R^9$ is tert-butyl; or (c) treatment with tributyltinhydride and acetic acid in the presence of catalytic bis(triphenylphosphine) palladium (II) chloride where $R^9$ is allyl.

If $R^9$ is benzyl, deprotection is performed by hydrogenolysis in the presence of 10% palladium in ethanol at about 45 psi for about 3 hours. The final compound III is, thus, isolated as the corresponding cationic salt by filtration of the catalyst over diatomaceous earth, removal of the solvent and trituration with a non-hydroxylic solvent, such as diethyl ether, diisopropyl ether, ethyl acetate, 1,4-dioxane or tetrahydrofuran. Compound III is utilized, as described below in Scheme III, for preparation of DPP-IV inhibitor compounds of Formula I.

SCHEME III

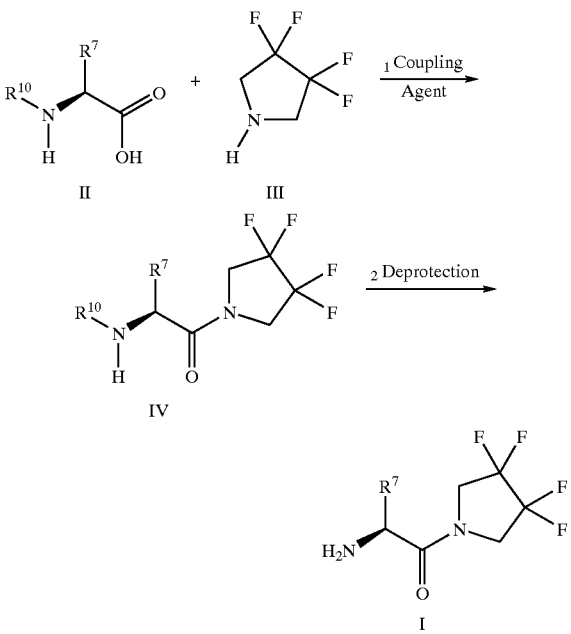

According to Scheme III, the compounds of Formula I may be prepared (Step 1) by coupling 3,3,4,4-tetrafluoropyrrolidine hydrochloride, compound of Formula III, with (L) amino acid compounds of Formula II (e.g., (L)-Boc-isoleucine, (L)-Boc-cyclohexylgycine, (L)-Boc-allo-isoleucine, (L)-Boc-leucine, (L)-Boc-valine or (L)-Boc-alanine), wherein $R^7$ is defined above and $R^{10}$ is a nitrogen-protecting group compatible with the above-described chemical Scheme III. For example, suitable nitrogen-protecting groups may include, but are not limited to, tert-butoxycarbonyl ("Boc"), benzyloxycarbonyl and fluorenylmethoxycarbonyl ("Fmoc"). Other examples of nitrogen-protecting groups are described in "Protective Groups in Organic Synthesis", $2^{nd}$. Ed., P. G. M. Wuts and T. W. Greene, p.315, incorporated herein by reference. When the coupling is performed using a compound of Formula II, the immediate product is a compound of Formula IV. The compound of Formula IV, in Step 2, may be dissolved and deprotected by methods appropriate to the nature of the $R^{10}$ group, as described in the reference cited above (e.g. gaseous acid if $R^{10}$ is Boc), providing a compound of Formula I.

The coupling reaction described above is readily accomplished by dissolving the compound of Formula II and a compound of Formula III in a reaction inert solvent (e.g. dichloromethane) in the presence of base (e.g. triethylamine or pyridine). To the resulting solution, is added a coupling agent or combination of coupling agents (e.g. hydroxybenzotriazole/1-(-3-dimethylaminopropyl)-3-ethylcarbodiimide hydrochloride). Other coupling agents may be utilized, such as 1-hydroxy-7-azabenzotriazole/1-(-3-dimethylaminopropyl)-3-ethylcarbodiimide hydrochloride, hydroxybenzotriazole/dicyclohexylcarbodiimide, 2-ethoxy-1-ethoxycarbonyl-1,2-dihydroquinoline, carbonyldiimidazole or diethylphosphorylcyanide. The coupling is conducted in an inert solvent, preferably an aprotic solvent. Suitable solvents include, for example, acetonitrile, dichloromethane, dimethylformamide, chloroform. For a discussion of other conditions useful for coupling carboxylic acids see Houben-Weyl, Vol XV, part II, E. Wunsch, Ed., G. Theime Verlag, 1974, Stuttgart, and those described in M. Bodansky, Principles of Peptide Synthesis, Springer-Verlag Berlin 1984, and The peptides. Analysis, Synthesis and Biology (ed. E. Gross and J. Meienhofer), vols 1–5 (Academic Press NY 1979–1983). The text of the above references are incorporated by reference.

The reaction is generally conducted at ambient pressure and temperatures, until the starting materials are no longer present as determined by thin layer chromatography or other analytical techniques well known to those skilled in the art. The coupled product of Formula IV may be isolated according to methods well known to those skilled in the art.

One of ordinary skill in the art will appreciate that the protected (L) amino acid compound of Formula II depicted in Scheme III, and exemplified in Examples 2–8, may be replaced with a racemic mixture of a compound of Formula II. Consequently, the compounds of Formula I may exist as racemic mixtures of enantiomers and these mixtures are within the scope of this invention.

The optically active amino acids may be obtained by resolution or by asymmetric synthesis or by other methods well known to those skilled in the art, prior to coupling in Step 1 of Schemes III. Alternatively, resolution, if so desired, may occur at a later point in the synthesis of the compounds of Formula I.

The compounds of Formula I of the present invention are useful for the treatment of dipeptidyl peptidase-IV related conditions; the treatment of type II diabetes mellitus (primary indication); the prevention of disease progression in type II diabetes mellitus; the treatment of type I diabetes, impaired glucose tolerance, hyperglycemia, impaired glucose tolerance, metabolic syndrome (Syndrome X or insulin resistance syndrome), glucosuria, metabolic acidosis, cataracts, diabetic neuropathy and nephropathy, Metabolic Syndrome, obesity, the treatment of hypertension, hyperlipidemia, metabolic acidosis, arthritis, osteoporosis, osteopenia, frailty, bone loss, bone fracture, short stature due to growth hormone deficiency, infertility due to polycystic ovary syndrome and short bowel syndrome.

The DPP-IV inhibitor compounds may be used in therapeutic methods for treating or preventing the above described conditions in a mammal, wherein a compound of Formula I of this invention is administered as part of an appropriate dosage regimen designed to obtain the benefits of the therapy. The appropriate dosage regimen, the amount of each dose administered and the intervals between doses of the compound will depend upon the compound of Formula I of this invention being used, the type of pharmaceutical compositions being used, the characteristics of the subject being treated and the severity of the conditions.

General Experimental Procedures

Melting points were determined on a Thomas Scientific capillary melting point apparatus, and are uncorrected.

NMR data were generated on a UNITYplus 400 spectrometer. Proton chemical shifts are reported in parts per million with tetramethylsilane as the standard ($\delta=0$). Fluorine chemical shifts are reported in parts per million with fluortrichloromethane as the standard ($\delta=0$).

Flash chromatography was performed according to the method described by W. C. Still et al. in *J. Org. Chem.* 1978, 43, 2923.

The examples below are intended to illustrate particular embodiments of the invention and are not intended to limit the specification, including the claims, in any manner.

EXAMPLE 1

Preparation of 3,3,4,4-tetrafluoropyrrolidine Hydrochloride

Step 1: Trifluoro-methanesulfonic Acid 2,2,3,3-tetrafluoro-4-(trifluoro-methanesulfonyloxy)-butyl Ester To a cooled (about 0° C.) solution of 2,2,3,3-tetrafluorobutanediol (15 grams, 93 mmol) and pyridine (19 mL, 230 mmol) in dichloromethane (250 mL), was added dropwise trifluoromethanesulfonic anhydride (34 mL, 200 mmol). After the addition, the mixture was stirred at about 0° C. for about one hour, followed by stirring at room temperature for one additional hour, then diluted with dichloromethane, washed with water and brine, dried over magnesium sulfate, filtered and concentrated to near dryness, leaving a dichloromethane-containing oil. $^1$H NMR (400 MHz, CDCl$_3$) $\delta$ 4.82 (m). $^{19}$F NMR (376 MHz, CDCl$_3$) $\delta$ −120.83 (m, 4H), −74.38 (s, 6H).

Step 2: 1-Benzyl-3,3,4,4-tetrafluoro-pyrrolidine Hydrochloride

A solution of the crude trifluoro-methanesulfonic acid, 2,2,3,3-tetrafluoro-4-(trifluoro-methanesulfonyloxy)-butyl ester, benzylamine (10 mL, 93 mmol) and triethylamine (33 mL, 230 mmol) in ethanol (230 mL) was heated to reflux overnight. The mixture was concentrated to about one-third of its volume, diluted with ether, washed with 1 N sodium hydroxide, water and brine, dried over magnesium sulfate, filtered and concentrated to an oil. The oil was redissolved in ether, cooled to about 0° C. and saturated with hydrogen chloride. The precipitate was collected and dried (23.8 grams, 95%, (melting point: 139–143° C.). $^{1}$H NMR (400 MHz, D$_{2}$O)4.05 (m, 4H), 4.41 (s, 2H), 7.26–7.41 (m, 5H). $^{19}$F NMR (376 MHz, D$_{2}$O) δ–118.42 (t, J=13.2 Hz).

Step 3: 3,3,4,4-Tetrafluoro-pyrrolidine Hydrochloride

A solution of 1-benzyl-3,3,4,4-tetrafluoro-pyrrolidine hydrochloride (23.8 grams, 88 mmol) in ethanol (300 mL) containing 10% palladium on carbon was treated with hydrogen in a Parr shaker at 45 psi for 3 hours. The mixture was filtered through Celite®, the filtrate was concentrated to dryness. The residue was triturated with ether and the solid was collected and dried (13.4 grams, 85%, (melting point: 193–196° C.). $^{1}$H NMR (400 MHz, D$_{2}$O) 3.93 (m, 4H), 7.26–7.41 (m, 5H). $^{19}$F NMR (376 MHz, D$_{2}$O) δ–122.25 (m)

EXAMPLE 2

(2S,3S)-2-Amino-3-methyl-1-(3,3,4,4-tetrafluoro-pyrrolidin-1-yl)-pentan-1-one

Step 1: [(1S,2S)-2-Methyl-1-(3,3,4,4-tetrafluoro-pyrrolidine-1-carbonyl)-butyl]-carbamic Acid tert-butyl Ester To a mixture of (L)-Boc-isoleucine (322 mg, 1.30 mmol), 3,3,4,4-tetrafluoro-pyrrolidine hydrochloride (300 mg, 1.67 mmol), hydroxybenzotriazole (225 mg, 1.67 mmol) and triethylamine (0.23 mL, 1.67 mmol) in dichloromethane (10 mL) was added 1-(-3-dimethylaminopropyl)-3-ethylcarbodiimide hydrochloride (319 mg, 1.67 mmol). The mixture was stirred at room temperature overnight, diluted with ethyl acetate, washed with 2 N Hydrochloric acid, saturated sodium bicarbonate solution, water and brine, dried over magnesium sulfate and concentrated. The product was purified by flash-chromatography (4:1 ratio of hexane/ethyl acetate) and isolated as a white solid (415 mg, 86%).

Step 2: (2S, 3S)-2-Amino-3-methyl-1-(3,3,4,4-tetrafluoro-pyrrolidin-1-yl)-pentan-1-one Hydrochloride

[(1S,2S)-2-Methyl-1-(3,3,4,4-tetrafluoro-pyrrolidine-1-carbonyl)-butyl]-carbamic acid tert-butyl ester (200 mg, 0.56 mmol) was dissolved in ethyl acetate (4 mL), cooled to about 0° C. and treated with gaseous hydrochloric acid for about 1 minute. After about 15 minutes at about 0° C. and about 30 minutes at room temperature, the mixture was concentrated to dryness and the solid was triturated with hexane, collected and dried under vacuum overnight (124 mg, 76%, melting point: greater than 250° C.).

EXAMPLE 3

(S)-2-Amino-2-cyclohexyl-1-(3,3,4,4-tetrafluoro-pyrrolidin-1-yl)-ethanone

Step 1: (S)-[1-Cyclohexyl-2-oxo-2-(3,3,4,4-tetrafluoro-pyrrolidin-1-yl)-ethyl]-carbamic Acid tert-butyl Ester (S)-[1-cyclohexyl-2-oxo-2-(3,3,4,4-tetrafluoro-pyrrolidin-1-yl)-ethyl]-carbamic acid tert-butyl ester was prepared from (L)-Boc-cyclohexylglycine and 3,3,4,4-tetrafluoropyrrolidine as analogously described in Step 1 of Example 1.

Step 2: (S)-2-Amino-2-cyclohexyl-1-(3,3,4,4-tetrafluoro-pyrrolidin-1-yl)-ethanone (S)-2-Amino-2-cyclohexyl-1-(3,3,4,4-tetrafluoro-pyrrolidin-1-yl)-ethanone was obtained by hydrochloric acid treatment of (S)-[1-cyclohexyl-2-oxo-2-(3,3,4,4-tetrafluoro-pyrrolidin-1-yl)-ethyl]-carbamic acid tert-butyl ester as analogously described in Step 2 of Example 1. (melting point: 278° C.).

EXAMPLE 4

(2S,3R)-2-Amino-3-methyl-1-(3,3,4,4-tetrafluoro-pyrrolidin-1-yl)-pentan-1-one

Step 1: [(1S,2R)-2-Methyl-1-(3,3,4,4-tetrafluoro-pyrrolidine-1-carbonyl)-butyl]-carbamic Acid tert-butyl Ester

[(1S,2R)-2-Methyl-1-(3,3,4,4-tetrafluoro-pyrrolidine-1-carbonyl)-butyl]-carbamic acid tert-butyl ester was prepared as analogously described in Step 1 of Example 1 from (L)-Boc-allo-isoleucine and 3,3,4,4-tetrafluoropyrrolidine.

Step 2: (2S,3R)-2-Amino-3-methyl-1-(3,3.4,4-tetrafluoro-pyrrolidin-1-yl)-pentan-1-one (2S,3R)-2-Amino-3-methyl-1-(3,3,4,4-tetrafluoro-pyrrolidin-1-yl)-pentan-1-one was prepared by Hydrochloric acid treatment of [(1S,2S)-2-methyl-1-(3,3,4,4-tetrafluoro-pyrrolidine-1-carbonyl)-butyl]-carbamic acid tert-butyl ester as analogously described in Step 2 of Example 1. (melting point: greater than 250° C.).

EXAMPLE 5

(S)-2-Amino-3-methyl-1-(3,3,4,4-tetrafluoro-pyrrolidin-1-yl)-butan-1-one (S)-2-Amino-3-methyl-1-(3,3,4,4-tetrafluoro-pyrrolidin-1-yl)-butan-1-one was prepared from (L)-Boc-valine and 3,3,4,4-tetrafluoropyrrolidine as analogously described in Example 1 (melting point: 234–238° C.).

EXAMPLE 6

(S)-2-Amino-4-methyl-1-(3,3,4,4-tetrafluoro-pyrrolidin-1-yl)-pentan-1-one hydrochloride (S)-2-Amino-4-methyl-1-(3,3,4,4-tetrafluoro-pyrrolidin-1-yl)-pentan-1-one hydrochloride was prepared from (L)-Boc-leucine and 3,3,4,4-tetrafluoropyrrolidine as analogously described in Example 1 (melting point: greater than 250° C.).

EXAMPLE 7

(S)-2-Amino-1-(3,3,4,4-tetrafluoro-pyrrolidin-1-yl)-propan-1-one Hydrochloride (S)-2-Amino-1-(3,3,4,4-tetrafluoro-pyrrolidin-1-yl)-propan-1-one hydrochloride was prepared from (L)-Boc-alanine and 3,3,4,4-tetrafluoropyrrolidine as analogously described in Example 1 (melting point: greater than 250° C.).

What is claimed is:

1. A process for preparing a compound of Formula I,

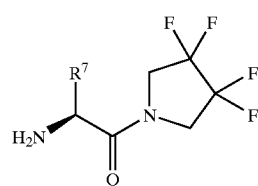

wherein $R^{7}$ is $(C_{1}-C_{8})$alkyl or $(C_{3}-C_{8})$cycloalkyl, comprising:

(a) treating an N-protected amino acid of the formula II,

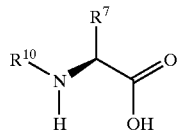

II wherein $R^7$ is $(C_1-C_8)$alkyl or $(C_3-C_8)$cycloalkyl and $R^{10}$ is a nitrogen-protecting group, with a base and 3,3,4,4-tetrafluoropyrrolidine hydrochloride in the presence of a coupling agent to form a coupled amino acid intermediate; and (b) deprotecting the coupled amino acid intermediate to form a compound of Formula I.

2. A process of claim 1 wherein $R^{10}$ is tert-butoxycarbonyl, benzyloxycarbonyl or fluorenylmethoxy-carbonyl.

3. A process of claim 1 wherein the N-protected amino acid is (L)-Boc-isoleucine, (L)-Boc-cyclohexylgycine, (L)-Boc-allo-isoleucine, (L)-Boc-leucine, (L)-Boc-valine or (L)-Boc-alanine.

4. A process of claim 1 wherein the coupling agent is 1-(-3-dimethylaminopropyl)-3-ethylcarbodiimide hydrochloride, dicyclohexylcarbodiimide, 2-ethoxy-1-ethoxycarbonyl-1,2-dihydroquinoline, carbonyldiimidazole or diethylphosphorylcyanide.

5. A process of claim 2 wherein the coupling agent is 1-(-3-dimethylaminopropyl)-3-ethylcarbodiimide hydrochloride, dicyclohexylcarbodiimide, 2-ethoxy-1-ethoxycarbonyl-1,2-dihydroquinoline, carbonyldiimidazole or diethylphosphorylcyanide.

6. A process of claim 3 wherein the coupling agent is 1-(-3-dimethylaminopropyl)-3-ethylcarbodiimide hydrochloride, dicyclohexylcarbodiimide, 2-ethoxy-1-ethoxycarbonyl-1,2-dihydroquinoline, carbonyldiimidazole or diethylphosphorylcyanide.

7. A process of claim 4 wherein the base in step (a) is triethylamine.

8. A process of claim 5 wherein the base in step (a) is triethylamine.

9. A process of claim 6 wherein the base in step (a) is triethylamine.

10. A process of claim 7 wherein the coupled amino acid intermediate is deprotected with gaseous hydrochloric acid.

11. A process of claim 8 wherein the coupled amino acid intermediate is deprotected with gaseous hydrochloric acid.

12. A process of claim 9 wherein the coupled amino acid intermediate is deprotected with gaseous hydrochloric acid.

13. A process of claim 10 further comprising purifying the coupled amino acid intermediate of step (a).

14. A process of claim 11 further comprising purifying the coupled amino acid intermediate of step (a).

15. A process of claim 12 further comprising purifying the coupled amino acid intermediate of step (a).

\* \* \* \* \*